(12) United States Patent
Mitsui et al.

(10) Patent No.: US 6,410,810 B1
(45) Date of Patent: Jun. 25, 2002

(54) HANDLING METHOD OF (FLUOROARYL) BORANE COMPOUND AND PREPARING METHOD OF HYDROCARBON SOLUTION

(75) Inventors: Hitoshi Mitsui, Kitakatsuragi-gun; Tsunemasa Ueno, Ikeda; Ikuyo Ikeno, Osaka; Naoko Hirano, Nishinomiya, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/512,289

(22) Filed: Feb. 24, 2000

Related U.S. Application Data

(63) Continuation-in-part of application No. 09/145,335, filed on Sep. 1, 1998, now abandoned.

(30) Foreign Application Priority Data

Sep. 18, 1997 (JP) ............................................. 9-253830

(51) Int. Cl.⁷ ............................... C07C 7/20; C07F 5/02
(52) U.S. Cl. ..................... 585/2; 585/3; 585/7; 585/13; 585/20; 585/24; 568/1; 568/6
(58) Field of Search ............................ 568/1, 6; 585/2, 585/3, 7, 13, 20, 24

(56) References Cited

U.S. PATENT DOCUMENTS 6,118,026 A * 9/2000 Mitsui et al. .................. 569/6

FOREIGN PATENT DOCUMENTS

EP 0604963 7/1994

OTHER PUBLICATIONS

J. L. W. Pohlmann and R. E. Brinckmann, "Preparation and Characterization of Group III A Derivatives", *Zeitschrift für Naturforschung*, 20b, pp 5–11 (1965). No month.

* cited by examiner

*Primary Examiner*—Elizabeth D. Wood
(74) *Attorney, Agent, or Firm*—Birch, Stewart, Kolasch & Birch, LLP

(57) ABSTRACT

A mixture of bis- and tris(fluoroaryl)borane compounds expressed by General Formula (1) below is handled in the form of a slurry made with a hydrocarbon solvent:

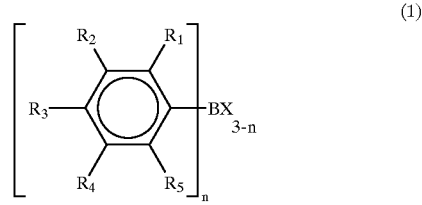

(1)

where each of $R_1$, $R_2$, $R_3$, $R_4$ and $R_5$ independently represents a hydrogen atom, a fluorine atom, a hydrocarbon group, or an alkoxy group provided that at least one of $R_1$–$R_5$ represents a fluorine atom, X represents a fluorine atom, a chlorine atom, a bromine atom, or an iodine atom, and wherein n represents 2 for the bis(fluoroaryl)borane compounds and 3 for the tris(fluoroaryl)borane compounds. Then, a hydrocarbon solution of the (fluoroaryl)borane compounds having a concentration of the tris(fluoroaryl)borane compounds in a range between 1 wt % and 1 wt % is prepared by dissolving the slurry into a hydrocarbon solvent in a virtually air-tight vessel. Consequently, it has become possible to provide a method of handling the tris(fluoroaryl) borane compounds in an industrially and economically advantageous manner, and a method of preparing the hydrocarbon solution of the tris(fluoroaryl)borane compounds readily and quickly without lowering the purity.

2 Claims, No Drawings

HANDLING METHOD OF (FLUOROARYL) BORANE COMPOUND AND PREPARING METHOD OF HYDROCARBON SOLUTION

This application is a continuation-in-part of application Ser. No. 09/145,335 filed on Sep. 1, 1998, now abandoned the entire contents of which are hereby incorporated by reference.

FIELD OF THE INVENTION

The present invention relates to a handling method of (fluoroaryl)borane compounds, such as tris(fluoroaryl) borane and bis(fluoroaryl)boryl halide, serving as, for example, a useful co-catalyst for a metallocene catalyst (polymeric catalyst) used in a cation complex polymerization reaction, and to a preparing method of a hydrocarbon solution of the (fluoroaryl)borane compound.

BACKGROUND OF THE INVENTION

Tris(fluoroaryl)borane, especially tris(pentafluorophenyl) borane, is a useful compound as a co-catalyst for promoting activity of a metallocene catalyst (polymeric catalyst) used in a cation complex. polymerization reaction, for example. The metallocene catalyst has been receiving considerable attention as a polyolefin polymeric catalyst.

For example, Z. Naturforsch., 20b, 5 (1965) discloses a method of letting pentafluorophenyl magnesium bromide and a boron trifluoride diethyl ether complex undergo a Grignard reaction in a chained ether solvent as a method of obtaining the above tris(pentafluorophenyl) borane.

Generally, the (fluoroaryl)borane compound, such as tris(pentafluorophenyl)borane obtained in the above method, is handled in the form of a hydrocarbon solution.

However, the solubility of the (fluoroaryl)borane compound, such as tris(pentafluorophenyl)borane, in the hydrocarbon solvent, especially an unsaturated hydrocarbon solvent, is relatively small at a normal temperature. Thus, when the (fluoroaryl)borane compound is stored (preserved), transported, transferred, or used, the (fluoroaryl)borane compound is handled in the form of a hydrocarbon solution prepared to have a concentration of the (fluoroaryl)borane compound in a range between 2 wt % and 4 wt %. Therefore, a large vessel or device is required to handle the (fluoroaryl)borane compound, which becomes critical disadvantages in terms of industrial and economical benefits.

To solve the above problems, the (fluoroaryl)borane compound may possibly be handled in the form of a solid (powders).

However, a solid (powders) of the (fluoroaryl)borane compound has a solubility as low as 1 wt % or so in the hydrocarbon solvent, especially an unsaturated hydrocarbon solvent, at a normal temperature. Thus, when a hydrocarbon solution having a suitable concentration for the use as a raw material in producing a catalyst for polyolefin polymerization is prepared as the aforementioned co-catalyst, more specifically, when a hydrocarbon solution having a concentration of 2 wt %–4 wt % is prepared, for example, a solid (powders) of the (fluoroaryl)borane compound is mixed with the hydrocarbon solvent, after which the resulting mixture must be kept at high temperatures over a long period to dissolve the compound into the solvent. Also, since the mixture is heated for a long period to dissolve the (fluoroaryl)borane compound into the solvent at high temperatures, a decomposition reaction, deterioration, quality alternation or the like of the (fluoroaryl)borane compound occurs during the process, thereby lowering the purity of the (fluoroaryl)borane compound.

Further, the presence of water triggers the decomposition reaction of the (fluoroaryl)borane compound. Thus, if moisture in the air enters into a solid (powders) of the (fluoroaryl) borane compound, for example, the purity of the (fluoroaryl) borane compound drops. Moreover, a solid (powders) of the (fluoroaryl)borane compound has poor fluidity. For this reason, a special device or the like is required to handle a solid (powders) of the (fluoroaryl)borane compound while completely removing moisture in the air, for example.

As has been discussed above, when the (fluoroaryl)borane compound is made into a solid (powders), its handling becomes too complicated and there arises a problem that the handling is critically disadvantageous in terms of industrial and economical benefits. Thus, there has been an increasing need for a handling method of the (fluoroaryl)borane compound, with which the (fluoroaryl)borane compound can be handled in an industrially and economically advantageous manner, and a preparing method of a hydrocarbon solution of the (fluoroaryl)borane compound, with which the hydrocarbon solution can be prepared readily and quickly without lowering the purity of the (fluoroaryl)borane compound.

SUMMARY OF THE INVENTION

It is therefore an object of the present invention to provide a handling method of the (fluoroaryl)borane compound, with which the (fluoroaryl)borane compound can be handled in an industrially and economically advantageous manner, and a preparing method of a hydrocarbon solution of the (fluoroaryl)borane compound, with which the hydrocarbon solution can be prepared readily and quickly without lowering the purity of the (fluoroaryl)borane compound.

The inventors of the present invention conducted an assiduous study on the handling method of the (fluoroaryl) borane compound and the preparing method of the hydrocarbon solution. In due course, the inventors discovered that, when the (fluoroaryl)borane compound is handled in the form of slurry made with a hydrocarbon solvent A, a smaller vessel or device can be used compared with a case of handling the same in the form of a solution, thereby making it possible to handle the (fluoroaryl)borane compound in an industrially and economically advantageous manner. Also, the inventors achieved the present invention when they discovered that a hydrocarbon solution having a concentration of the (fluoroaryl)borane compound in a range between 1 wt % and 10 wt % can be readily and quickly prepared without lowering the purity of the (fluoroaryl)borane compound by dissolving the above slurry into a hydrocarbon solvent B in a virtually air-tight vessel.

To achieve the above and other objects, a handling method of the (fluoroaryl)borane compound of the present invention is characterized in that a (fluoroaryl)borane compound expressed by General Formula (1) below is handled in the form of slurry made with a hydrocarbon solvent A:

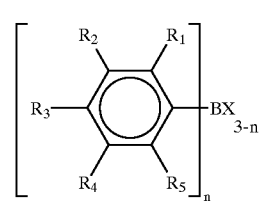

(1)

where each of $R_1$, $R_2$, $R_3$, $R_4$, and $R_5$ independently represents a hydrogen atom, a fluorine atom, a hydrocarbon group, or an alkoxy group provided that at least one of $R_1$–$R_5$ represents a fluorine atom, X represents a fluorine atom, a chlorine atom, a bromine atom, or an iodine atom, and n represents 2 or 3.

According to the above method, compared with a case of handling the (fluoroaryl)borane compound in the form of a solution, a smaller vessel or device can be used by handling the same in the form of the slurry. Consequently, it has become possible to handle the (fluoroaryl)borane compound in an industrially and economically advantageous manner. Further, for example, when the hydrocarbon solution is filtered at a temperature at which the (fluoroaryl)borane compound does not crystallize undissolved components (impurities), such as magnesium halide, contained in the hydrocarbon solution can be separated/removed as the filtration residue. Therefore, the (fluoroaryl)borane compound can be handled in the form of pure slurry.

Also, to achieve the above and other objects, the preparing method of the hydrocarbon solution of the (fluoroaryl) borane compound of the present invention is characterized in that a hydrocarbon solution having a concentration of the (fluoroaryl)borane compound in a range between 1 wt % and 10 wt % is prepared by dissolving the above slurry into a hydrocarbon solvent B in a virtually air-tight vessel.

According to the above method, since the (fluoroaryl) borane compound has been already made into the slurry with the hydrocarbon solvent A, the (fluoroaryl)borane compound dissolves into the hydrocarbon solvent B quickly. In other words, it is not necessary to heat the mixture for a long period to dissolve the (fluoroaryl)borane compound into the solvent at high temperatures. Consequently, it has become possible to prepare a hydrocarbon solution having a concentration of the (fluoroaryl)borane compound in a range between 1 wt % and 10 wt % readily and quickly without lowering the purity of the (fluoroaryl)borane compound.

The present invention includes, in part, the combination of tris)fluoroaryl)borane and bis(fluoroaryl)borane in solid, slurry or liquid form, a method of preparing this combination and its use.

Further objects, features, advantages of the present invention will be fully understood by the following description. Also, the benefits of the present invention will be apparent from the following explanation.

DESCRIPTION OF THE EMBODIMENTS

A handling method of the (fluoroaryl)borane compound expressed by General Formula (1) above of the present invention is a method of handling the (fluoroaryl)borane compound in the form of slurry made with a hydrocarbon solvent A. Also, a preparing method of a hydrocarbon solution of the (fluoroaryl)borane compound expressed by General Formula (1) above of the present invention is a method of preparing a hydrocarbon solution having a concentration of the (fluoroaryl)borane compound in a range between 1 wt % and 10 wt A% by dissolving the above slurry into a hydrocarbon solvent B in a virtually air-tight vessel.

In the present invention, the expression "handle the (fluoroaryl)borane compound" means the handling of the (fluoroaryl)borane compound when it is stored (preserved), transported, transferred, or used (including the process of preparing the hydrocarbon solution). Also, in the present invention, the phrase "in the form of slurry" or the term "slurry" includes the case where the (fluoroaryl)borane compound exists in the hydrocarbon solvent A in the form of a so-called cake.

The (fluoroaryl)borane compound to be handled in the present invention expressed by the above formula is a compound, in which each of the substituents denoted as $R_1$, $R_2$, $R_3$, $R_4$, and $R_5$ is independently a hydrogen atom, a fluorine atom, a hydrocarbon group, or an alkoxy group, provided that at least one of the substituents denoted as $R_1$–$R_5$ is a fluorine atom, the substituent denoted as X is a fluorine atom, a chlorine atom, a bromine atom, or an iodine atom, and n is 2 or 3. Thus, when n=2, the (fluoroaryl)borane compound is bis(fluoroaryl)boryl halide, and when n=3, the (fluoroaryl)borane compound is tris(fluoroaryl)borane.

Examples of the hydrocarbon group include: an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the handling method and preparing method of the present invention. Examples of such a functional group include: a methoxy group, a methylthio group, an N,N-dimethylamino group, an o-anise group, a p-anise group, a trimethylsilyl group, a t-butyldimethylsilyloxy group, a trifluoromethyl group, etc.

The alkoxy group is expressed by General Formula (A):

$$-OR_a \qquad (A)$$

where $R_a$ represents a hydrocarbon group. Examples of the hydrocarbon group denoted as $R_a$ in the formula include: an aryl group, a straight-chain, branched-chain, or cyclic alkyl group having up to 12 carbon atoms, a straight-chain, branched-chain, or cyclic alkenyl group having 2–12 carbon atoms. The hydrocarbon group may further include a functional group that remains inactive to the handling method and preparing method of the present invention.

Examples of the alkoxy group expressed by General Formula (A) above include: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

The (fluoroaryl)borane compound can be obtained by, for example, reacting an adequate kind of a (fluoroaryl) magnesium derivative with boron halide in an ether solvent or the like. If a mole ratio of the (fluoroaryl)magnesium derivative and boron halide is set adequately, either of bis(fluoroaryl)boryl halide or tris(fluoroaryl)borane can be obtained selectively.

The slurry of the (fluoroaryl)borane compound made with the hydrocarbon solvent A can be readily obtained by a so-called solvent exchange technique to exchange an ether solvent with the hydrocarbon solvent A. To be more specific, an ether solution of the (fluoroaryl)borane compound is mixed with the hydrocarbon solvent A, while the ether solvent is being distilled out, and the resulting hydrocarbon solution is filtered at a temperature at which the (fluoroaryl) borane compound does not crystalize, after which the filtrate is cooled in a virtually air-tight vessel. Examples of the ether solvent include, but not limited: chained ethers, such as dimethyl ether, diethyl ether, dipropyl ether, diisopropyl ether, dibutyl ether, diisobutyl ether, dipentyl ether, diisopentyl ether, 1, 2-dimethoxy ethane, 1,2-diethoxy ethane, and di-2-methoxy ethyl ether; cyclic ethers, such as tetrahydrofuran, tetrahydropyrane and 1,4-dioxane; etc. The manufacturing method of the (fluoroaryl)borane compound is not especially limited.

Examples of bis(fluoroaryl)boryl halide include: bis (pentafluorophenyl)boryl halide, bis(2,3,4,6-tetrafluorophenyl)boryl halide, bis(2,3,5,6-tetrafluorophenyl)boryl halide, bis(2,3,5-trifluorophenyl) boryl halide, bis(2,4,6-trifluorophenyl)boryl halide, bis(1,3-difluorophenyl)boryl halide, bis(2,3,5,6-tetrafluoro-4-methylphenyl)boryl halide, bis(2,3,4,6-tetrafluoro-5- methylphenyl)boryl halide, bis(2,4,5-trifluoro-6-methylphenyl)boryl halide, bis(2,3,6-trifluoro-4-methylphenyl)boryl halide, bis(2,4,6-trifluoro-3-methylphenyl)boryl halide, bis(2,6-difluoro-3-methylphenyl)boryl halide, bis(2,4-difluoro-5-methylphenyl)boryl halide, bis(3,5-difluoro-2-methylphenyl)boryl halide, bis(4-methoxy-2,3,5,6-tetrafluorophenyl)boryl halide, bis(3-methoxy-2,4,5,6-tetrafluorophenyl)boryl halide, bis(2-methoxy-3,5,6-trifluorophenyl)boryl halide, bis(3-methoxy-2,5,6-trifluorophenyl)boryl halide, bis(3-methoxy-2,4,6-trifluorophenyl)boryl halide, bis(2-methoxy-3,5-difluorophenyl)boryl halide, bis(3-methoxy-2,6-difluorophenyl)boryl halide, bis(3-methoxy-4,6-difluorophenyl)boryl halide, bis(2-methoxy-4,6-difluorophenyl)boryl halide, bis(4-methoxy-2,6-difluorophenyl)boryl halide, etc.

Examples of tris(fluoroaryl)borane include: tris (pentafluorophenyl)borane, tris(2,3,4,6-tetrafluorophenyl) borane, tris(2,3,5,6 -tetrafluorophenyl)borane, tris(2,3,5-trifluorophenyl)borane, tris(2,4,6-trifluorophenyl)borane, tris(1, 3-difluorophenyl)borane, tris(2,3,5,6-tetrafluoro-4-methylphenyl)borane, tris(2,3, 4, 6-tetrafluoro-5-methylphenyl)borane, tris(2,4,5-trifluoro-6-methylphenyl) borane, tris(2,3,6-trifluoro-4-methylphenyl)borane, tris(2,4, 6-trifluoro-3-methylphenyl)borane, tris(2,6-difluoro-3-methylphenyl)borane, tris(2,4-difluoro-5-methylphenyl) borane, tris(3,5-difluoro-2-methylphenyl)borane, tris(4-methoxy-2,3,5,6-tetrafluorophenyl)borane, tris(3-methoxy-2,4,5,6-tetrafluorophenyl)borane, tris(2-methoxy-3,5,6-trifluorophenyl)borane, tris(3-methoxy-2,5,6-trifluorophenyl)borane, tris(3-methoxy-2,4,6-trifluorophenyl)borane, tris(2-methoxy-3,5-difluorophenyl) borane, tris(3-methoxy-2,6-difluorophenyl)borane, tris(3-methoxy-4,6-difluorophenyl)borane tris(2-methoxy-4,6-difluorophenyl)borane, tris(4-methoxy-2,6-difluorophenyl) borane, etc. Of all these example compounds, tris (pentafluorophenyl)borane is particularly suitable.

The hydrocarbon solvent A used in the handling method of the present invention is not especially limited as long as being an inactive non-aqueous solvent having a higher boiling point than the ether solvent, for example. The hydrocarbon solvent B used in the preparing method of the present invention is not especially limited as long as being an inactive non-aqueous solvent. The hydrocarbon solvents A and B can be either identical or different from each other.

Examples of the hydrocarbon solvent A/B include, but not limited to: straight-chain, branched-chain, or cyclic aliphatic hydrocarbons, such as pentane, isopentane, hexane, cyclohexane, methyl cyclohexane, ethyl cyclohexane, heptane, octane, nonane, decane, undecane, dodecane, tridecane, tetradecane, pentadecane, hexadecane, octadecane, paraffin, and petroleum ether; aromatic hydrocarbons, such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethyl benzene, propylbenzene, and butylbenzene; etc. The aliphatic hydrocarbon and aromatic hydrocarbon may further include a functional group inactive to the handling method and preparing method of the present invention. One member or a mixture of two or more members selected from these example hydrocarbon solvents can be used effectively. Of all these example hydrocarbon solvents, hexane, cyclohexane, methyl cyclohexane, ethyl cyclohexane, heptane, octane, IsoparE of Exxon Corp. (a mixture of isoparaffins having approximately 10 carbon atoms), nonane, decane, octadecane, etc. are more suitable than the others.

The boiling point of the hydrocarbon solvent A is not especially limited, but it is preferably 60° C. or above, and more preferably 80° C. or above. In case that a mixed hydrocarbon solvent is used as the hydrocarbon solvent A, the boiling point is defined as the lowest boiling point among the boiling points of all the compounds included.

The slurry of the (fluoroaryl)borane compound made with the hydrocarbon solvent A can be readily obtained by: (1) mixing an ether solution of the (fluoroaryl)borane compound with the hydrocarbon solvent A while distilling out the ether solvent; (2) filtering the resulting hydrocarbon solution at a temperature at which the (fluoroaryl)borane compound does not crystallize; (3) and cooling the filtrate in a virtually air-tight vessel. Besides the ether solvent, the ether solution of the (fluoroaryl)borane compound may optionally include other kinds of solvents, such as the hydrocarbon solvent. In other words, the ether solution of the (fluoroaryl)borane compound of the present invention may be a reaction solution obtained by reacting an adequate kind of a (fluoroaryl)magnesium derivative with boron halide in a solvent including the ether solvent. Note that the preparing method of the slurry of the (fluoroaryl)borane compound with the hydrocarbon solvent A is not limited to the above disclosed method.

The method of mixing the ether solution of the (fluoroaryl)borane compound with the hydrocarbon solvent A while distilling out the ether solvent is not especially limited, and example methods are: a method of distilling out the ether solvent after the hydrocarbon solvent A is mixed with the ether solution; a method of distilling out the ether solvent while the ether solution is being dropped to the hydrocarbon solvent A; a method of distilling out the ether solvent while the hydrocarbon solvent A is being dropped to the ether solution; etc. The ether solvent can be distilled out under a normal (atmospheric) pressure or decreasing pressure.

An amount of the (fluoroaryl)borane compound contained in the hydrocarbon solution when it is filtered, that is, a concentration of the (fluoroaryl)borane compound, is not especially limited. However, a concentration as high as possible is preferred, so that the slurry can be handled in a more advantageous manner. To be more specific, it is preferable that the concentration of the (fluoroaryl)borane compound is almost a saturation concentration at the temperature when the hydrocarbon solution is filtered. Containing the (fluoroaryl)borane compound in the hydrocarbon solution above the saturation concentration is not preferable because a part of the (fluoroaryl)borane compound is separated as the filtration residue.

Undissolved components (impurities), such as magnesium halide, produced as a by-product when synthesizing the (fluoroaryl)borane compound and contained in the hydrocarbon solution, can be separated/removed as the residue by filtering the hydrocarbon solution at a temperature at which the (fluoroaryl)borane compound does not crystalize. Consequently, the (fluoroaryl)borane compound can be handled in the form of pure slurry.

The filtering method is not especially limited, and decompression filtration and filtration under pressure, etc. can be used. The temperature of the hydrocarbon solution when it is filtered is not especially limited as long as it is below the boiling point of the hydrocarbon solvent A under a pressure applied during the filtration. However, a higher temperature is preferable to carry out the filtration more efficiently. To be more specific, a temperature in a range between 0° C. and 200° C. is more preferable and a temperature in a range between 30° C. and 150° C. is further preferable. Also, it is preferable that the temperature of the hydrocarbon solution is maintained so as not to drop during the filtration to suppress the crystallization of the (fluoroaryl)borane compound.

By cooling the filtrate obtained by the above filtration in a virtually air-tight vessel, the (fluoroaryl)borane compound is crystallized, whereby slurry of the (fluoroaryl)borane compound made with the hydrocarbon solvent A is obtained. The temperature of the cooled filtrate can be below the temperature of the hydrocarbon solution when it is filtered as long as the hydrocarbon solvent A does not coagulate. An amount of the filtrate charged to the vessel with respect to a capacity thereof is not especially limited; however, it is preferable to charge (fill) the filtrate to the vessel so as to leave the least space inside.

The virtually air-tight vessel used in the present invention is not especially limited. However, a vessel equipped with a nozzle for circulating the content, namely the slurry (or hydrocarbon solution), is preferable, and examples of which include: installation type tanks, such as a tank equipped with an internal heating coil and a tank equipped with external heating cylinder; portable tanks, such as a tank wagon, a tank rolly, and a bulk container; etc.

An amount of the (fluoroaryl)borane compound contained in the slurry varies depending on a combination of the (fluoroaryl)borane compound and hydrocarbon solvent A and temperatures. However, to handle the (fluoroaryl)borane compound in a more efficient manner while it is stored (preserved), transported, transferred, or used (including the process of preparing the hydrocarbon solution), an amount in a range between 5 wt % and 90 wt % is preferable, an amount in a range between 6 wt % and 80 wt % is more preferable, and an amount in a range between 7 wt % and 70 wt % is particularly preferable.

It is preferable that a space inside the vessel is in an atmosphere where moisture and oxygen that trigger a decomposition reaction, the deterioration or quality alteration of the (fluoroaryl)borane compound are almost completely removed, for example, in an inert gas atmosphere, such as a nitrogen gas, a helium gas, and an argon gas. The temperature of the slurry inside the vessel, that is, the temperature of the slurry when it is stored (preserved), transported, transferred, or used, is not especially limited. However, it is preferable to maintain the temperature of the slurry at or below 50° C. to suppress the decomposition reaction of the (fluoroaryl)borane compound.

As has been explained, according to the method of the present invention, by handling the (fluoroaryl)borane compound in the form of the slurry made with the hydrocarbon solvent A, a smaller vessel or device can be used compared with a case of handling the same in the form of a solution. Consequently, it has become possible to handle the (fluoroaryl)borane compound in an industrially and economically advantageous manner.

Also, a hydrocarbon solution having a concentration of the (fluoroaryl)borane compound in a range between 1 wt % and 10 wt % can be prepared by dissolving the above slurry into the hydrocarbon solvent B in a virtually air-tight vessel. It is preferable that the hydrocarbon solvent B, into which the slurry is dissolved, is identical with the hydrocarbon solvent A forming the slurry. A vessel used when preparing the hydrocarbon solution and a vessel used for handling the slurry may be identical or different from each other. Alternatively, after the slurry is handled and dissolved into the hydrocarbon solvent B in the same vessel, the resulting hydrocarbon solution may be transferred to another vessel to adjust a concentration of the (fluoroaryl)borane compound to a desired level. Note that when the slurry is handled with a vessel and transferred to another vessel to prepare the hydrocarbon solution, it is preferable to carry out this process in an inert gas atmosphere.

A method of mixing the slurry with the hydrocarbon solvent B while dissolving the former into the latter is not especially limited, and example methods are: a method of dissolving the slurry into the hydrocarbon solvent B after the slurry and the hydrocarbon solvent B are mixed with each other; a method of dissolving the slurry into the hydrocarbon solvent B while the former is being added to the latter; a method of dissolving the slurry into the hydrocarbon solvent B while the latter is being added to the former; etc. The slurry can be dissolved into the hydrocarbon solvent B by heating the vessel, namely the content, with stirring. A heating temperature to heat the content is not especially limited. Also, a pressure inside the vessel can be a normal (atmospheric), decreasing, or increasing pressure. Note that the preparing method of the hydrocarbon solution of the (fluoroaryl)borane compound is not limited to the above disclosed methods.

The slurry is handled while being dissolved into the hydrocarbon solvent B by the following method, for example. That is, the slurry is injected into a portable tank, such as a tank rolly and a bulk container, equipped with nozzles inside the upper portion and lower portion, after which the portable tank is transported to the destination. Then, the hydrocarbon solvent B is injected to the portable tank at the destination, after which the content is circulated inside the portable tank while the portable tank is kept heated. In other words, an example method of preparing the hydrocarbon solution of the (fluoroaryl)borane compound is a method of adding the hydrocarbon solvent B to the slurry in the portable tank at the destination where the hydrocarbon solution will be used, and then the content is circulated while the portable tank is kept heated.

As has been discussed above, according to the method of the present invention, since the (fluoroaryl)borane compound is in the form of the slurry made with the hydrocarbon solvent A, the (fluoroaryl)borane compound dissolves into the hydrocarbon solvent B quickly. In other words, it is not necessary to heat the hydrocarbon solution for a long period to dissolve the (fluoroaryl)borane compound into the hydrocarbon solution at high temperatures. Consequently, it has become possible to prepare a hydrocarbon solution having a concentration of the (fluoroaryl)borane compound in a range between 1 wt % and 10 wt %, preferably between 2 wt % and 4 wt %, readily and quickly without lowering the purity.

In the above method, the slurry is dissolved into the hydrocarbon solvent B in a virtually air-tight vessel. Hence, the occurrence of a decomposition reaction, the deterioration or quality alteration of the (fluoroaryl)borane compound caused by the heating over a long period, moisture or oxygen can be suppressed. Consequently, it has become possible to maintain the purity of the (fluoroaryl)borane compound. Also, in the above method, for example, a special device for completely removing moisture in the air used when handling a solid (powders) of the (fluoroaryl)borane compound can be omitted. Thus, the preparing method of the present invention has excellent operability and handling properties, and therefore, attains excellent preparing efficiency in preparing the hydrocarbon solution of the (fluoroaryl)borane compound. Here, the concentration can be set to a desired level by adjusting a used amount of the hydrocarbon solvents A and B.

The present invention includes, in part, the combination of tris(fluoroaryl)borane and bis(fluoroaryl)borane in solid, slurry or liquid form, a method of preparing this combination and its use. The bis(fluoroaryl)borane can be in amounts associated with impurities, and is preferably in a molar ratio of 0.0001 to 1 of bis(fluoroaryl)borane to tris(fluoroaryl) borane. More preferably, the ratio is 0.001 to 0.25 and most preferably is 0.025 to 0.2.

The following explanation of the increased solubility of tris(fluoroaryl)borane in the presence of bis(fluoroaryl) borane is presented as a hypothesis, and is not to be misconstrued as limiting the present invention in any way.

It appears that the presence of bis(fluoroaryl)borane (even at concentrations associated with impurities) enhances the solubility of tris(fluoroaryl)borane.

The following facts support this hypothesis:

1) when tris(pentafluorophenyl)borane is produced, 5–10 wt % of bis(pentafluorophenyl)borane-fluoride is also produced as a by-product;
2) bis(pentafluorophenyl)borane-fluoride still remains in the hydrocarbon solution of tris(pentafluorophenyl) borane after it is subjected to solvent exchange; and
3) tris(pentafluorophenyl)borane containing a large volume of bis(pentafluorophenyl)borane-fluoride has a high solubility with respect to the hydrocarbon solvent.

When tris(pentafluorophenyl)borane is isolated and purified as a solid by means of filtration or the like, bis (pentafluorophenyl)borane-fluoride is separated and removed from tris(pentafluorophenyl)borane. As a result, the solubility of isolated and purified tris(pentafluorophenyl) borane drops significantly.

From the above, it is presumed that a bis (pentafluorophenyl)borane compound affects the solubility of tris(pentafluorophenyl)borane with respect to the hydrocarbon solvent.

In the following, the present invention will be explained in detail by way of examples and a comparative example, but the present invention is not limited to the disclosure below.

EXAMPLE 1

To begin with, air inside a reaction vessel equipped with a thermometer, a dropping funnel, a stirrer, a nitrogen gas conduit, and a Dimroth condenser is displaced by a nitrogen gas satisfactorily. Then, 8.4315 g (59.4 mmol) of a boron trifluoride diethyl ether complex serving as boron halide and 65 ml of diethyl ether (ether solvent) are charged to the reaction vessel. Meanwhile, 113.9 g of a diethyl ether solution including 176.3 mmol of pentafluorophenyl magnesium bromide serving as a (fluoroaryl)magnesium derivative is charged to the dropping funnel.

Then, the diethyl ether solution is dropped to the content (boron halide solution) with stirring at room temperature over 80 minutes under a nitrogen gas atmosphere, during which a temperature inside the reaction vessel has reached a reflux temperature. When the dropping ends, the reaction solution is let undergo reaction (maturation) at the reflux temperature for 3 hours with stirring under a nitrogen gas atmosphere, whereby a diethyl ether solution of tris (pentafluorophenyl)borane as the (fluoroaryl)borane compound is obtained.

Subsequently, 266 g of IsoparE (a commodity name, hydrocarbon solvent A) is charged to a distilling vessel equipped with a thermometer, a dropping funnel, a stirrer, a nitrogen gas conduit, and a Liebig condenser. The end of the outlet of the Liebig condenser is kept open and a receiver is placed at a predetermined position. Meanwhile, the diethyl ether solution of tris(pentafluorophenyl)borane is charged to the dropping funnel.

Then, IsoparE is heated to 96° C. with stirring under a nitrogen gas flow, to which the diethyl ether solution in the dropping funnel is dropped over 60 minutes. Subsequently, diethyl ether distilled out during the dropping is removed under a normal pressure. When the dropping ends, the content (mixture) in the distilling vessel is heated to 123° C., whereby 221.5 g of a solvent including diethyl ether is distilled out in total.

After the solvent including diethyl ether is distilled out, the content is cooled to 95° C. Meanwhile, air inside a filter equipped with a pressure gauze, a nitrogen gas conduit, a receiver, and a discharge line is displaced by a nitrogen gas satisfactorily, after which the filter is maintained at 95° C.–100° C. Then, the content is supplied to the filter and subjected to filtration under pressure with heating by applying a pressure with a nitrogen gas, so that magnesium bromide fluoride as a by-product (crystals) is separated and removed, whereby 182.3 g of filtrate is obtained. The filtrate is kept at 50° C., so that tris(pentafluorophenyl)borane does not crystalize.

Then, 26.2 g of the filtrate is transferred to a vessel, in which the air has been displaced by a nitrogen gas satisfactorily, and cooled to 25° C. Consequently, slurry of tris(pentafluorophenyl)borane made with IsoparE is obtained in the form of a so-called cake.

The cake is analyzed by $^{19}$F-NMR. More specifically, $^{19}$F-NMR is measured under predetermined conditions using p-fluorotoluene as an internal standard reagent. Then, a peak integral of a fluorine atom of p-fluorotoluene, and a peak integral of fluorine atoms at the ortho-position of a pentafluorophenyl group in tris(pentafluorophenyl)borane are computed from the resulting $^{19}$F-NMR chart first, and thence a weight of tris(pentafluorophenyl)borane is computed using the above two peak integrals. As a result, it turns out that the cake contains 14.1 wt % of tris (pentafluorophenyl)borane. In other words, an amount of tris(pentafluorophenyl)borane contained in the slurry is 14.1 wt %.

Then, the slurry is mixed with 100.24 g of IsoparE (a commodity name, hydrocarbon solvent B), after which the resulting mixture is heated to 40° C. Then, the slurry dissolves into IsoparE quickly, whereby an IsoparE solution of tris(pentafluorophenyl)borane is obtained.

A concentration of tris(pentafluorophenyl)borane in the IsoparE solution measured in the above manner using $^{19}$F-NMR is 2.92 wt %. Also, a purity of tris(pentafluorophenyl) borane is 94.7% (area ratio). Thus, the yield of tris (pentafluorophenyl)borane is computed as 85.3%.

An amount of residual diethyl ether contained in the IsoparE solution is measured by measuring $^{1}$H-NMR. To be more specific, $^{1}$H-NMR is measured under predetermined conditions using p-fluorotoluene as an internal standard reagent. A peak integral of a hydrogen atom of a methylene group in diethyl ether, a peak integral of a hydrogen atom of a methyl group in p-fluorotoluene, a peak integral of a fluorine atom of p-fluorotoluene, and a peak integral of fluorine atoms at the ortho-position of a pentafluorophenyl group in tris(pentafluorophenyl)borane are computed from the resulting $^{1}$H-NMR chart and the above-obtained $^{19}$F-NMR chart first, and thence a ratio of the residual diethyl ether with respect to tris(pentafluorophenyl)borane is computed using the above peak integrals. As a result, it turns out that a ratio of the residual diethyl ether with respect to tris(pentafluorophenyl)borane is 4.9 mol %.

EXAMPLE 2

A diethyl ether solution of tris(pentafluorophenyl)borane is obtained through the reaction and manipulation in the same manner as those in Example 1 above except that an amount of a boron trifluoride diethyl ether complex charged to the reaction vessel is reduced to 8.3887 g (59.1 mmol), and that 114.2 g of a diethyl ether solution containing 183.2 mmol of pentafluorophenyl magnesium bromide is charged to the dropping funnel.

Then, 250.1 g of n-octane (hydrocarbon solvent A) is charged to a distilling vessel of the same type as the one used in Example 1 above. The end of the outlet of the Liebig condenser is kept open and a receiver is placed at a predetermined position. Meanwhile, the diethyl ether solution of tris(pentafluorophenyl)borane is charged to the dropping funnel.

Then, n-octane is heated to 94° C. with stirring under a nitrogen gas flow, after which the diethyl ether solution in the dropping funnel is dropped over 90 minutes. Then, diethyl ether distilled out during the dropping is removed under a normal pressure. When the dropping ends, the content (mixture) in the distilling vessel is heated to 126° C., whereby 225.6 g of a solvent including diethyl ether is distilled out in total. When the distillation of the solvent containing diethyl ether ends, the content is cooled to 96° C. Meanwhile, air inside a filter of the same type as the one used in Example 1 above is displayed by a nitrogen gas satisfactorily, after which the filter is maintained at 98° C.–100° C. Then, the content is supplied to the filter and subjected to filtration under pressure with heating by applying a pressure with a nitrogen gas, so that magnesium bromide fluoride is separated and removed, whereby 178.4 g of filtrate is obtained. The filtrate is maintained at 50° C., so that tris(pentafluorophenyl)borane does not crystalize.

Then, 5.86 g of the filtrate is transferred to a vessel, in which the air has been displaced by a nitrogen gas satisfactorily, after which the filtrate is cooled to 25° C. Consequently, slurry of tris(pentafluorophenyl)borane made with n-octane is obtained in the form of a so-called cake. The cake is analyzed in the same manner as Example 1 above, and it turns out that the cake contains 15.9 wt % of tris(pentafluorophenyl)borane, meaning that an amount of tris(pentafluorophenyl)borane contained in the slurry is 15.9 wt %.

Then, the slurry is mixed with 23.14 g of n-octane (hydrocarbon solvent B), after which the mixture is heated to 42° C. Then, the slurry dissolves into n-octane quickly, whereby an n-octane solution of tris(pentafluorophenyl)borane is obtained.

A concentration and a purity of tris(pentafluorophenyl)borane in the n-octane solution analyzed in the same manner as Example 1 above are 3.15 wt % and 93.9% (area ratio), respectively. Thus, the yield of tris(pentafluorophenyl)borane is computed as 91.9%. Also, an amount of the residual diethyl ether contained in the n-octane solution is measured in the same manner as Example 1 above, and it turns out that a ratio of the residual diethyl ether with respect to tris(pentafluorophenyl)borane is 1 mol % or less.

EXAMPLE 3

Slurry of tris(pentafluorophenyl)borane made with n-octane (hydrocarbon solvent A) is obtained in the form of a so-called cake using 7.84 g of the filtrate obtained in Example 2 above through the same manipulation as that in Example 2 above. Like the cake obtained in Example 2 above, it turns out that the cake obtained herein contains 15.9 wt % of tris(pentafluorophenyl)borane, meaning that an amount of tris(pentafluorophenyl)borane contained in the slurry is 15.9 wt %.

Then, the slurry is mixed with 30.68 g of IsoparE (hydrocarbon solvent B), after which the mixture is heated to 38° C. Then, the slurry dissolves into IsoparE quickly, whereby an IsoparE solution (a mixed solution of IsoparE and n-octane) of tris(pentafluorophenyl)borane is obtained.

A concentration and a purity of tris(pentafluorophenyl)borane in the IsoparE solution analyzed in the same manner as Example 1 above are 3.18 wt % and 93.9% (area ratio), respectively. Thus, the yield of tris(pentafluorophenyl)borane is computed as 92.0%. Also, an amount of the residual diethyl ether contained in the IsoparE solution is measured in the same manner as Example 1 above, and it turns out that a ratio of the residual diethyl ether with respect to tris(pentafluorophenyl)borane is 1 mol % or less.

Comparative Example 1

Here, 0.4963 g (purity: 99%, area ratio) of powders of tris(pentafluorophenyl)borane and 16.0878 g of IsoparE are charged to a vessel, in which the air has been displaced by a nitrogen gas satisfactorily, after which the mixture is stirred for 3 hours or so at 28° C. with stirring. However, tris(pentafluorophenyl)borane does not dissolve into IsoparE completely.

Thus, the content (mixture) is heated, and tris(pentafluorophenyl)borane has dissolved into IsoparE completely when heated to 87° C. The resulting solution is allowed to stand and cooled, and the solution starts to crystallized when cooled to 63° C. After the solution is cooled to room temperature, the supernatant is analyzed in the same manner as Example 1 above using $^{19}$F-NMR. Consequently, a concentration and a purity of tris(pentafluorophenyl)borane are 0.91 wt % and 83.0% (area ratio).

Thus, it is revealed that the conventional preparing method, in which powders of tris(pentafluorophenyl)borane are dissolved into IsoparE with heating, the purity of tris(pentafluorophenyl)borane drops and the IsoparE solution of tris(pentafluorophenyl)borane can not be prepared in a stable manner.

As was shown by Comparative Example 1, the solubility with respect to IsoparE (hydrocarbon solvent) of the isolated and purified tris(pentafluorophenyl)borane having a purity of 99% was 0.91 wt % at 25° C. That is, this specific value is the inherent solubility of tris(pentafluorophenyl)borane with respect to IsoparE at 25° C.

In contrast, in the case of tris(pentafluorophenyl)borane containing 5.3 wt % of bis(pentafluorophenyl)borane-fluoride and having a purity of 94.7%, the solubility thereof with respect to IsoparE at 25° C. increases to 4.5 wt % (Experimental Example 2). In other words, it is presumed that the solubility of tris(pentafluorophenyl)borane with respect to IsoparE at 25° C. increases because of the presence of bis(pentafluorophenyl)borane-fluoride. However, the reason why the presence of bis(pentafluorophenyl)borane-fluoride increases the solubility to such a superior level cannot be expected from the prior art.

When tris(pentafluorophenyl)borane is isolated and purified as a solid, bis(pentafluorophenyl)borane-fluoride is separated and removed from the tris(pentafluorophenyl)borane. This highly-pure tris(pentafluorophenyl)borane has an inherently low solubility. Thus, if a hydrocarbon solution is prepared using highly-pure tris(pentafluorophenyl)borane, the hydrocarbon solvent has to be heated to high temperature to dissolve the highly-pure tris(pentafluorophenyl)borane. This heating to high temperatures is deleterious since it causes the purity of tris(pentafluorophenyl)borane to drop.

In contrast, when tris(pentafluorophenyl)borane is handled in the form of slurry made with the hydrocarbon solvent, bis(pentafluorophenyl)borane-fluoride is not separated or removed, and therefore, the bis(pentafluorophenyl)borane-fluoride coexists with tris(pentafluorophenyl)borane. Thus, the solubility of tris(pentafluorophenyl)borane is increased by the action of bis(pentafluorophenyl)borane-fluoride. Consequently, when the hydrocarbon solution is prepared by using tris(pentafluorophenyl)borane in the form of slurry, the procedure can be performed at low temperatures, thereby making it unnecessary to heat the hydrocarbon solvent at high temperatures. In addition, because the hydrocarbon solvent is not heated to high temperatures, the purity of tris(pentafluorophenyl)borane does not drop.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of preparing a hydrocarbon solution of a mixture of bis- and tris(fluoroaryl)borane compounds expressed as:

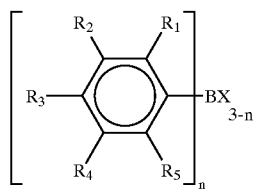

(1)

where each of $R_1$, $R_2$, $R_3$, $R_4$, and $R_5$ independently represents one of a hydrogen atom, a fluorine atom, a hydrocarbon group, and an alkoxy group provided that at least one of $R_1$–$R_5$ represents a fluorine atom, X represents one of a fluorine atom, a chlorine atom, a bromine atom, and an iodine atom, and wherein n represents 2 for the bis(fluoroaryl)borane compounds and 3 for the tris(fluoroaryl)borane compounds, wherein a hydrocarbon solution of said (fluoroaryl)borane compounds having a concentration of said tris(fluoroaryl)borane compounds in a range between 1 wt % and 10 wt % is prepared by combining said (fluoroaryl)borane compounds with a hydrocarbon solvent A to form a slurry, containing a mixture of (fluoroaryl)borane compounds having both n=2 and n=3, and then dissolving said slurry into a hydrocarbon solvent B in a virtually air-tight vessel.

2. A method for preparing a hydrocarbon solution of bis- and tris(fluoroaryl)borane compounds expressed as:

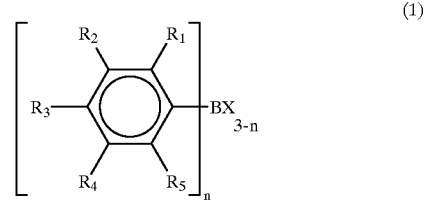

(1)

where each of $R_1$, $R_2$, $R_3$, $R_4$, and $R_5$ independently represents one of a hydrogen atom, a fluorine atom, a hydrocarbon group, and an alkoxy group provided that at least one or $R_1$–$R_5$ represents a fluorine atom, X represents one of a fluorine atom, a chlorine atom, a bromine atom, and an iodine atom, and wherein n represents 2 for the bis(fluoroaryl)borane compounds and 3 for the tris(fluoroaryl)borane compounds, wherein a hydrocarbon solution of said (fluoroaryl)borane compound having a concentration of said (fluoroaryl)borane compounds in a range between 1 wt % and 10 wt % is prepared by combining said (fluoroaryl)borane compounds with a hydrocarbon solvent A to form a slurry, and then dissolving said slurry into a hydrocarbon solvent B in a virtually air-tight vessel.

* * * * *